United States Patent [19]

Saska

[11] Patent Number: 4,670,587
[45] Date of Patent: Jun. 2, 1987

[54] PROCESS FOR REDUCING THE 4-CARBOXYBENZALDEHYDE CONTENT OF A CRUDE TEREPHTHALIC ACID PRODUCT

[75] Inventor: Michael Saska, Baton Rouge, La.

[73] Assignee: Louisiana State University and Agricultural and Mechanical College, Baton Rouge, La.

[21] Appl. No.: 825,521

[22] Filed: Feb. 3, 1986

[51] Int. Cl.$^4$ .............................................. C07C 51/42
[52] U.S. Cl. ...................................... 562/485; 562/486
[58] Field of Search .................................. 562/485, 486

[56] References Cited

U.S. PATENT DOCUMENTS

| 3,330,863 | 7/1967 | Read et al. | 562/487 |
| 3,362,989 | 1/1968 | McMakin et al. | 562/487 |
| 3,526,658 | 9/1970 | Bryant | 562/487 |
| 3,658,894 | 4/1972 | Joveland et al. | 562/487 |

*Primary Examiner*—Natalie Trousof
*Assistant Examiner*—Vera C. Clarke
*Attorney, Agent, or Firm*—Edgar E. Spielman, Jr.

[57] ABSTRACT

This invention relates to a process for the purification of crude terephthalic acid. The process includes heating the crude acid on a first plate and locating a second plate adjacent the first plate whereby vapors emanating from the crude acid form a sublimate on the second plate. The principal impurity removed is 4-carboxybenzaldehyde. The crude acid produced is applied to the first plate as a layer having a thickness of about 2 to about 5 mms thick and heated to a temperature of from about 180° to about 220° C. The upper plate is not heated except by the convective heat transfer and the heat of sublimation provided by the vapor moving from the crude acid layer to the second plate.

10 Claims, 3 Drawing Figures

PROCESS FOR REDUCING THE 4-CARBOXYBENZALDEHYDE CONTENT OF A CRUDE TEREPHTHALIC ACID PRODUCT

BACKGROUND OF THE INVENTION

This invention relates to the purification of a crude terephthalic acid product and, more particularly, to a process for substantially reducing the 4-carboxybenzaldehyde content of such product.

The growing commercial importance of terephthalic acid is significant. Polyesterification of this acid yields polyethylene terephthalate which is utilized in the production of fibers, tapes and injection-blow molded articles.

The economic production of terephthalic acid by the partial oxidation of p-xylene has been demonstrated. While this route to terephthalic acid is widely used, it produces a crude product which contains a number of impurities, most of which are incomplete oxidation products and which are more volatile than the terephthalic acid product. Of these impurities, 4-carboxybenzaldehyde is the most troublesome as it acts as a chain terminator during the polyesterification of the acid and, either alone or in combination with other intermediate oxidation products, has been found to give rise to undesirable colors in the resultant polyester product.

The oxidation of p-xylene generally yields a crude terephthalic acid product containing 0.1 to 3% 4-carboxybenzaldehyde. It is generally accepted in the polymer industry that the crude terephthalic acid product should not contain more than about 0.2% of this aldehyde impurity. Reducing the concentration of the 4-carboxybenzaldehyde impurity in the crude product is a difficult proposition since the aldehyde impurity and the terephthalic acid have similar molecular properties. Many purification schemes have been proposed.

In one purification procedure, the terephthalic acid is purified by forming a water-soluble alkali salt of the acid, e.g., diammonium or disodium terephthalate, and then contacting the salt with an aqueous solution containing activated carbon. The activated carbon acts to remove the incomplete oxidation products and metals from the terephthalic acid crude product. The terephthalic acid is regenerated by neutralization.

In another scheme, the crude terephthalic acid product is purified by first vaporizing the crude product in a carrier gas, such as superheated steam. After such vaporization is accomplished, the superheated steam-vapor mix is intimately contacted with a solid particulate terephthalic acid that is at a temperature sufficiently lower than the vaporous-mixture and in an amount sufficient to condense out from the vapor the terephthalic acid. After such condensation, there are two phases present, i.e., a solid phase, which comprises the condensed terephthalic acid and the solid particulate terephthalic acid used to effect such condensation, and a vapor phase which contains the more volatile impurities and the carrier gas. A simple separation of the two phases is then performed. An example of the foregoing is shown in U.S. Pat. No. 3,330,863.

Another scheme utilizes steam sublimation of the crude terephthalic acid product and is disclosed in U.S. Pat. No. 3,526,658. This purification scheme includes the continual feeding of finely divided solid particles of the crude terephthalic acid product into a gaseous entrainer stream. The product is fed in a non-tacky condition and the entrainer stream is flowing at a velocity sufficient to substantially immediately entrain and transport the particles. The terephthalic acid is vaporized while it is being carried in the entrainer stream. The carrier stream and its associated contents are indirectly heated to provide the before-mentioned required sublimation. After separating any remaining solid material from the carrier stream, the carrier stream is cooled to condense at least a substantial portion of the terephthalic acid vapor contained therein. It is noted that this cooling is such that a major portion of the more volatile materials in the carrier stream are not condensed. The condensed terephthalic acid product is removed from the gaseous carrier stream.

Oxidation of the 4-carboxybenzaldehyde impurity to produce more terephthalic acid is included in the process described in U.S. Pat. No. 3,658,894. In this process, the crude terephthalic acid product is heated to a temperature sufficient to cause sublimation thereof. The resultant vapor is captured in a reaction zone through which is passed a gas containing molecular oxygen. This molecular oxygen effects the before-mentioned oxidation of the 4-carboxybenzaldehyde.

Yet other purification techniques are disclosed in U.S. Pat. No. 3,362,989, the latter patent describing a fractional sublimation procedure.

A frequently used crude terephthalic acid product purification process employs terephthalic acid aging-recrystallization in a liquid environment of aqueous acetic acid at a temperature of about 285° C. and under elevated pressure. The aging-recrystallization occurs after at least a portion of the 4-carboxybenzaldehyde has been reduced to p-toluic acid by contact with a catalyst in a hydrogen atmosphere.

While all of the foregoing purification methods may be effective in removing 4-carboxybenzaldehyde from a crude terephthalic acid product, they all suffer from one or more of the following: (1) high energy requirements; (2) elaborate processing equipment; and (3) the use of additional chemicals.

Therefore, it is an object of this invention to provide a process for reducing the content of 4-carboxybenzaldehyde in a crude terephthalic acid product which process has a low energy requirement, is simple in operation and in equipment used and which does not use additional chemicals to achieve the purification.

THE INVENTION

The concentration of 4-carboxybenzaldehyde in crude terephthalic acid product is reduced in accordance with the process of this invention. This process comprises placing a dry crude terephthalic acid product layer on a first plate. The layer has an average thickness of from 2 to about 5 mm. A second plate is located above the crude terephthalic product layer at a distance within the range of from about 3 to about 10 mm whereby vapor from the crude terephthalic product layer will be captured on the second plate as sublimate. The second plate is unheated except for the heating resulting from the hot vapor contacting and sublimating on the second plate. The first plate is heated to a temperature within the range of from about 180° to about 220° C. for a period of time within the range of from about 20 to about 80 minutes. This heating will produce the before-mentioned vapor from the crude terephthalic acid product layer. The crude terephthalic acid product can be provided by any of the well known processes for the production of such acid.

In most commercial applications, the 4-carboxybenzaldehyde containing crude terephthalic acid product will be from the well known catalytic oxidation of p-xylene. In such catalytic oxidations, the p-xylene is used in the form of a dilute solution (e.g., 2 to 20%, preferably 7 to 12%) in a suitable solvent such as acetic, propionic, butyric acids or a mixture of said acids. An effective catalyst is a soluble cobalt salt, as in the form of cobalt acetate, propionate or butyrate or mixtures thereof, and in such an amount as to correspond to 0.1 to 1.0%, preferably 0.3 to 0.6%, by weight of cobalt metal based on the weight of fatty acid solvent. As a reaction activator, a methylenic ketone, such as methylethyl ketone, methyl n-propyl ketone, diethyl ketone, 2,4-pentanedione and 2,5-hexanedione, may be used, with methylethyl ketone being a preferred activator. Concentrations of the activator are generally at least about 1%, and preferably in the range of 3 to 10%, by weight of the fatty acid solvent. For highly efficient oxidation, it is preferred to have between about 1% and about 9% of water in the reaction mixture and the best results are generally obtained when the water content is in the range of 3% to 7%.

Oxidation is effected by contacting the reaction mixture with a gas containing molecular oxygen. The reaction is allowed to proceed generally for only a few minutes and, at most, for not more than about an hour or two, and being preferably terminated before all of the methyl groups of the p-xylene have been oxidized. This results not only in the efficient and rapid oxidation of the p-xylene to terephthalic acid but, also, in preserving a substantial portion of the ketone activator in the reaction mixture which, after suitable treatment, can be recycled to the oxidation reaction. The resultant terephthalic acid is isolated. To the filtered oxidation solution sufficient p-xylene, methylenic ketone activator and perhaps water are added to restore the starting composition so that it will be ready for oxidation (see U.S. Pat. No. 2,853,514 and U.S. Pat. No. 3,036,122). Generally, the crude terephthalic acid product from such processes will contain 4-carboxybenzaldehyde in an amount within the range of from about 1000 to about 10,000 ppm. (The process of this invention, however, is beneficial in cases where the 4-carboxybenzaldehyde concentration is as little as 200 ppm, though most generally, concentrations of 1000 to 1500 ppm will be encountered.) Other impurities such as metal compounds (ash) are usually present in amounts of about 100 to about 1000 ppm. If the metal compounds are volatilized by the process of this invention, a reduction in their concentration in the purified product will be realized. Those metal compounds not volatilized can be removed by subsequent conventional treatment if their concentration exceeds that permissible for the final product, e.g., magnetic tape produced from the purified terephthalic acid.

The crude terephthalic acid product should be dried before being placed on the first plate for the heating procedure in accordance with the subject process. The drying is most easily accomplished in a rotary kiln. Other drying techniques may be used as the need arises.

The first plate provides a planar surface onto which the crude terephthalic acid product is applied. The plate can be rectangular, circular, etc., with no criticality assigned to shape—indeed, the plate can be provided by the upper surface of continuous belt which is powered for movement between a set of pulleys. This latter plate configuration is useful when the process of the invention is operated in a continuous mode as hereinafter described. The plate is preferably of a metallic material, e.g., stainless steel.

Heating of the first plate is conveniently achieved with electrical heaters as such are easily adjusted to keep the plate within the 180° to about 220° C. temperature range. Heating by flame is also considered practical. It is an important feature of this invention that the above temperatures are below the sublimation temperature of terephthalic acid. Not only is an energy savings achieved by operating in this range, but also a tacky purified terephthalic acid is not realized. It is recognized that the tackiness of terephthalic acid frustrates the purification procedure in reducing the 4-carboxybenzaldehyde content as the 4-carboxybenzaldehyde has a tendency to condense as a film of liquid onto terephthalic acid thereby promoting an agglomeration of the terephthalic acid particles into rather sticky masses.

Not only is a relatively low temperature used by the process of this invention, but also it has been found that high purification is achieved even though only about 2 to about 3 weight percent of the original crude terephthalic acid product is volatilized.

Like the first plate, the second plate provides a planar surface. This planar surface faces the crude terephthalic acid layer and provides a surface onto which the vapors emanating from the crude terephthalic acid layer can sublimate. Also, like the first plate, the second plate can be of any of the before described materials of construction and of any convenient configuration. The second plate is preferably of the same type as that of the first plate. The second plate is unheated except for the convective heat and the heat of sublimation transferred to it via the vapor from the first plate. After thermal steady state is realized, the first plate will generally have a temperature 5° to 20° C. greater than that of the second plate. This difference in temperature between the plate provides a vertical temperature gradient from plate to plate. The vertical temperature gradient and the anisotropic nature of the terephthalic acid crystals are theorized, though the process of this invention is not bound by this theory, to provide for the substantially selective volatilization, from the crude terephthalic acid product, of the 4-carboxybenzaldehyde. It is observed that as the terephthalic acid in the crude product is heated, it changes crystalline structure from oval facetless crystals to conglomerated polygonal crystals. The former crystals are not allowable of escape, from the crystal lattice, of 4-carboxybenzaldehyde vapor while the latter crystals are. As the polygonal crystalline shape becomes dominate, more and more 4-carboxybenzaldehyde can escape. It has been found that some terephthalic acid will also volatilize. A portion will recrystallize on the polygonal terephthalic acid crystals as the vapor moves through the crystalline lattice while another portion will escape the crystalline lattice and recrystallize with the 4-carboxybenzaldehyde on the second plate.

The total recrystallization which occurs on the second plate comprises two types of crystalline structures. One type is small crystallites of about 5 microns size and contains terephthalic acid and about 50 weight percent 4-carboxybenzaldehyde. The other crystalline structures are dendrites of several hundreds of microns in length. These dendrites contain terephthalic acid and 4-carboxybenzaldehyde and have a 4-carboxybenzaldehyde concentration intermediate between that of the small crystallite and the purified terephthalic acid material on the first plate. Since the dendrite crystals contain a relatively high percentage of terephthalic acid, their recovery from the second plate is desirable. Preferential recovering of the dendrite crystals over the 4-carboxybenzaldehyde enriched smaller crystallites is satisfactorily achieved by mechanical methods. The brittleness and the size of the dendrite crystals allows for their preferential removal by the simple expedient of breaking them from the second plate with a stream of high velocity air. The air should not have too high a velocity, however, as the smaller crystallites may also be removed. Determination of the correct air velocity is best determined empirically by matching observed removal with a selected air velocity and determining if the removal effect is satisfactory.

The process of this invention is most conveniently carried out at ambient pressure, thus alleviating the need for vacuum or high pressure conditions.

These and other features of this invention contributing to satisfaction in use and economy in operation will be more fully understood from the following description of preferred embodiments of the invention when taken in connection with the accompanying drawings in which identical numerals refer to identical parts and in which.

Figure 1:
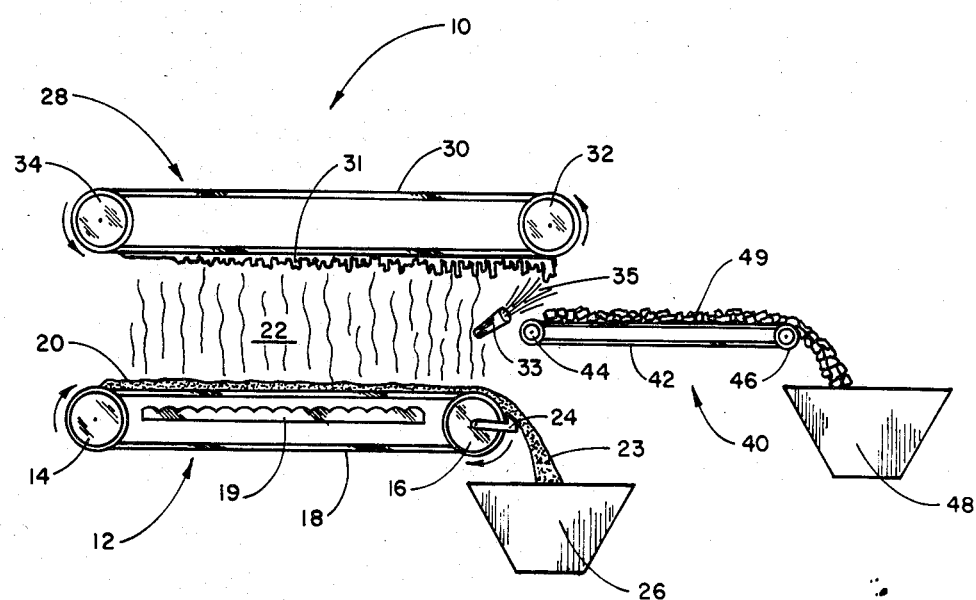
FIG. 1 is a schematic view of a process of this invention operated in the continuous mode.

Referring now to FIG. 1, there can be seen process equipment, generally designated by the numeral 10, for effecting the process of this invention continuously. Process equipment 10 comprises a first plate 12 which is provided by a metallic conveyor belt 18 which is operated by pulleys 14 and 16. Conveyor belt 18 has located beneath its upper surface electric heater 19.

Process equipment 10 also includes upper plate 28 which is provided by a metallic conveyor belt 30 which is driven by pulleys 32 and 34. Upper plate 28 is not heated except by the convective heat transfer caused by vapors emanating from crude terephthalic acid product 20. Located at the discharge end of conveyor belt 30 is air nozzle 33.

In operation, crude terephthalic acid product is continuously fed to the upper surface of conveyor belt 18. Heat is applied to conveyor belt 18 by electrical heater 19 so that crude terephthalic acid product 20 is heated to a temperature within the range of from about 180° to about 220° C. The lower surface of conveyor belt 30 is located directly above this heated acid product and at a distance within the range of from about 3 to about 10 mms. As crude terephthalic acid product 20 reaches process temperature, vapor 22 begins to evolve therefrom. Vapor 22 contacts the lower surface of conveyor belt 30 and forms a sublimate 31 thereon. Sublimate 31 is composed of very small crystallites and much larger dendrite crystals. As the sublimate reaches the discharge end of conveyor belt 30, which is generally after about 20 to about 80 minutes, it is impacted by a stream of air 35 provided by air nozzle 33, which stream has a velocity sufficient to break from the discharge end of conveyor belt 30 any dendrite crystals which may have formed on the lower surface. The removed dendrite crystals then fall to conveyor 40 which comprises conveyor belt 42 which is driven by pulleys 44 and 46.

Dendrite crystals 49 are discharged from conveyor 40 into storage hopper 48.

The purified terephthalic acid 23 is scraped by scraper 24 and discharged into storage hopper 26.

So that the crude terephthalic acid product is subjected to the desired temperature for a period of time in accordance with the process of this invention, the speeds of travel of conveyor belts 18 and 30 are adjusted so that the desired period of process time is achieved before discharging the purified terephthalic acid from conveyor belt 18.

Figure 2:
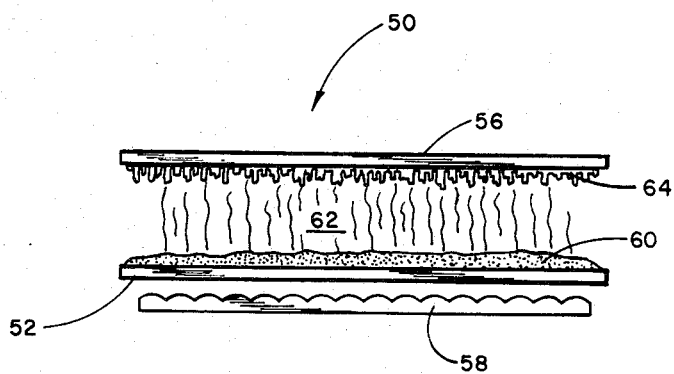
FIG. 2 is a schematic view of a process of this invention operated in the batch mode.

In FIG. 2, a schematic of the batch mode for the process of this invention is shown. For the batch process, process equipment, generally designated by the numeral 50, comprises a lower plate 52 and an upper plate 56. Plates 52 and 56 are located so that they provide a distance between the layer 60 of crude terephthalic acid product and the lower surface of upper plate 56 within the range of from about 3 to about 10 mm. Lower plate 52 is heated electrically by electric heater 58. Once layer 60 achieves the process temperature desired, i.e., that within the range of from about 180° to about 220° C., vapor evolving from layer 60 contacts the lower surface of plate 56 to collect thereon as a sublimate 64. Plate 56 is not heated except by the convective heat transfer heat of sublimation caused by the contact of vapor 62 with the lower surface of plate 56. Sublimate 64 formed on the lower surface of plate 56 is comprised of small crystallites and much larger dendrites. After the process time is completed, generally within the range of from about 20 to about 80 minutes, the upper plate is removed and the dendrite crystals are broken therefrom and collected for future use as a recycled material or as a feed to a process in which they would be useful. The now purified terephthalic acid found on the upper surface of plate 52 is scraped therefrom and is sent to storage or to further processing.

The following examples are merely illustrative of the present invention and not a limitation thereof.

EXAMPLE 1

Terephthalic acid samples with 4-carboxybenzaldehyde content in the range 200 to 7500 ppm were treated as follows. A layer of the dry crude terephthalic acid of about 2 mm thickness was placed on a bottom plate and heated electrically to about 200° C. A second unheated plate was positioned at the distance shown in Table I above the heated layer of terephthalic acid. The relationship of plate positions was maintained for 60 minutes. Subsequently, the material was collected from the first plate; the deposit on the second plate was separated by vibrating and scraping to form a fraction composed of small crystallites of about 5 um size that stuck relatively strongly to the plate and a fraction composed of large dendrites up to about 1 mm long that fell easily off of the plate. The samples were weighed and analyzed for 4-carboxybenzaldehyde using the method of Saska and Sturrock described in Anal. Chim. Acta 155 (1983) 343. The total weight of the deposit on the upper plate comprised about 3% of the weight of the initial material. The results are given in Table I.

Approximately 50 to 65% weight percent of 4-carboxybenzaldehyde was removed. The purification effect was found practically independent of the initial 4-carboxybenzaldehyde content and the particle size of the initial material.

TABLE 1

| Run No. | % CBA* Initially Present[1] | Lower Plate Temperature | Crude tpt** acid Average Thickness in mm | Distance Between Plates in mm | % CBA* Removed[2] | Average Particle Size of the Crude tpt** acid in μm |
| --- | --- | --- | --- | --- | --- | --- |
| 1 | 0.751 | 200° C. | 2 | 10 | 65 | 20 |
| 2 | 0.751 | 200° C. | 2 | 10 | 51 | 1 |
| 3 | 0.023 | 200° C. | 2 | 10 | 59 | 150 |
| 4 | 0.751 | 200° C. | 2 | 3 | 65 | 10 |
| 5 | 0.278 | 200° C. | 2 | 3 | 50 | 30 |

Figure 3:
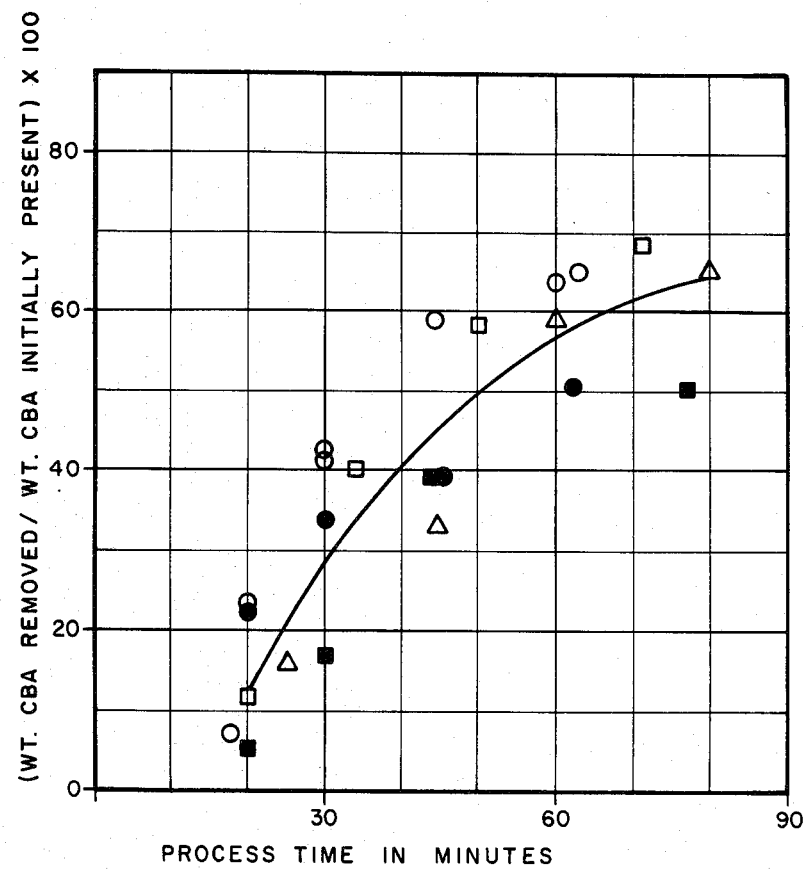
FIG. 3 is a plot of weight % of carboxybenzaldehyde removed vs. process time.

*CBA = 4-carboxybenzaldehyde
**tpt = terephthalic acid
[1] weight % of CBA based upon total weight of crude tpt.
[2] weight of CBA removed/weight of CBA initially present in crude tpt after a 60 min treatment The plot shown in FIG. 3 shows the change in rate of CBA removal with the passage of process time. The various data points correlate with the Run No.'s in Table I according to the following legend:

| Run No. | Symbol |
| --- | --- |
| 1 | ○ |
| 2 | ● |
| 3 | △ |
| 4 | □ |
| 5 | ■ |

The resultant curve obtained from the data points shows that the rate of CBA removal is highest initially and slowly decreases with the passage of process time thereby indicating an optimum process time after which continued processing will provide less than economical CBA removal. Generally, optimum process times are in the range of from about 50 to about 65 minutes.

I claim:

1. A process for reducing the 4-carboxybenzaldehyde content of a mix containing terephthalic acid and 4-carboxybenzaldehyde, said process comprising:
   (a) placing a layer of said mix on a first plate, said layer having an average thickness within the range of from about 2 to about 5 mm;
   (b) locating a second plate above said layer at a distance within the range of from about 3 to about 10 mm, to capture on said second plate, as sublimate, at least a portion of the vapor from said layer resulting from the heating in (c) said second plate being unheated except for the heat provided said vapor portion; and
   (c) heating said first plate to bring it to a temperature within the range of from about 180° to about 220° C. for a period of time within the range of from about 20 to about 80 minutes.

2. The process of claim 1 wherein the 4-carboxybenzaldehyde content of said mix is within the range of from about 50 to about 15,000 ppm.

3. The process of claim 1 wherein the average thickness of said layer is within the range of from about 2 to about 5 mm.

4. The process of claim 1 wherein said mix is the reaction product of the catalytic oxidation of p-xylene.

5. The process of claim 1 wherein the distance between said second plate and said layer is within the range of from about 3 to about 10 mm.

6. The process of claim 1 wherein, during said process, said first plate is at a temperature within the range of from about 5° to about 20° C. greater than the temperature of said second plate.

7. The process of claim 1 wherein said sublimate comprises dendrite crystals and small crystallites.

8. The process of claim 7 including the further step of selectively removing said dendrite crystals from said second plate subsequent to said period of time.

9. The process of claim 8 wherein said selective removal is effected by directing a stream of air on to said sublimate, said stream of air being a sufficient velocity to break said dendrite crystals from said second plate but not of sufficient velocity to break a substantial portion of said small crystallites from said second plate.

10. The process of claim 1 wherein said mix is dried prior to being placed on said first plate.

* * * * *

UNITED STATES PATENT AND TRADEMARK OFFICE
CERTIFICATE OF CORRECTION

PATENT NO. : 4,670,587

DATED : June 2, 1987

INVENTOR(S) : Michael Saska

It is certified that error appears in the above-identified patent and that said Letters Patent is hereby corrected as shown below:

Column 5, line 27, reads "mode; and", should read --mode;--.

Column 5, line 30, reads "batch mode.", should read --batch mode; and--.

Column 6, line 64, reads "65% weight percent", should read --65 weight percent--.

Column 7, line 49, Claim 1, reads "heating in (c) said", should read --heating in (c), said--.

Column 8, line 15, Claim 1, reads "heat provided said", should read --heat provided by said--.

Signed and Sealed this

Twenty-fourth Day of November, 1987

Attest:

DONALD J. QUIGG

*Attesting Officer*   *Commissioner of Patents and Trademarks*